United States Patent [19]
Farcasiu et al.

[11] Patent Number: 5,880,111
[45] Date of Patent: Mar. 9, 1999

[54] THERAPEUTIC DERIVATIONS OF DIPHOSPHONATES

[76] Inventors: Dan Farcasiu, 4729 Bayard St., Pittsburgh, Pa. 15213; John F. Hartmann, 1 Woodmeadow La., Princeton Junction, N.J. 08550; Pal Herczegh; Ferenc J. Sztaricskai, both of Debrecen, Hungary

[21] Appl. No.: 478,245

[22] Filed: Jun. 7, 1995

[51] Int. Cl.$^6$ .................. A61K 31/43; A61K 31/545; A61K 31/495; C07F 9/02; C07D 499/88; C07D 501/00; C07D 265/36; C07D 241/04

[52] U.S. Cl. .................. 514/79; 558/155; 558/162; 562/13; 540/215; 540/217; 540/300; 540/301; 540/302; 540/304; 540/308; 540/200; 544/23; 544/24; 544/105; 544/361; 514/80; 514/81; 514/82; 514/83; 514/84; 514/85; 514/86; 514/87; 514/88; 514/89; 514/90; 514/91; 514/92; 514/93; 514/94; 514/95; 514/96; 514/97; 514/98; 514/99; 514/100; 514/101

[58] Field of Search .................. 514/108, 79, 80, 514/81, 82–101; 544/105, 361; 540/215, 217, 300, 302, 304, 308, 200; 546/23, 24; 562/13; 558/155

[56] References Cited

U.S. PATENT DOCUMENTS 4,746,654  5/1988  Breliere et al. .......................... 514/108

*Primary Examiner*—Mukund J. Shah
*Assistant Examiner*—Pavanaram K Sripada
*Attorney, Agent, or Firm*—D. J. Perrella

[57] ABSTRACT

Novel chemotherapeutic agents having utility in treating infectious diseases such as periodontal disease, certain urinary tract infections, and infectious urinary tract stones, are obtained by combining chemically a diphosphonate compound with a therapeutic agent effective against the foregoing diseases.

14 Claims, No Drawings

THERAPEUTIC DERIVATIONS OF DIPHOSPHONATES

BACKGROUND OF THE INVENTION

Osteomyelitis is a painful and debilitating condition caused by a variety of micro-organisms, mainly *Staphylococcus aureus*. This disease occurs more commonly in children. Within the adult population, diabetics and kidney dialysis patients also are vulnerable. The acute form of the disease is treatable with antibiotics, but requires a lengthy period of daily therapy. It can, however, revert to a recurrent or chronic form requiring repeated hospital stays and treatment regimens. The remarks of Waldvogel et al. in their 1980 review continue to be relevant today:

"The high success rate observed with antibiotic therapy in most bacterial diseases contrasts with the substantial failure rate in the treatment of bone infections." (1980) *New Eng. J. Med.* 303:360.

Urinary catheters are the most common source of nosocomial infections. The bacteriuria which may result from the catheterization is serious because it is a predisposing factor to Gram-negative septicemia, a disease with a high rate of mortality. Kunin stated the consequences of this infectious nidus succinctly:

"Systemic antimicrobial therapy is ineffective in eradicating catheter-associated infections other than temporarily." (1987) *Detection, Prevention and Management of Urinary Tract Infections,* Chapt. 5, pp. 247–297.

Urinary calculi can develop anywhere in the urinary tract. They are hard, mineralized substances producing pain, obstructions and secondary infections. Basically there are two types of urinary stones: metabolic, originating through metabolic dysfunctions, and infectious, associated with bacterial infections. Infection persists in 40% of patients treated with antibiotics, and a full 60% of those develop recurring stones. Left untreated, infected calculi can result in kidney loss and even death in 25% of such cases. Some metabolic stones become contaminated and bacteria are entrapped within the interstices during its crystallization. Such infected stones are notoriously resistant to eradication. Current treatment of infectious urinary calculi involves surgical removal with concomitant administration of antimicrobial agents.

Broadly speaking, there are two categories of periodontal disease: gingivitis and periodontitis, both generated by micro-organisms in dental plaque on the tooth surface. Both conditions are characterized by an inflammation of the gingiva, the gum tissue at the base of the teeth. Periodontitis also involves bone erosion and loss of dentition over a long period of time. Burt (1992) *Clin. Geriat. Med.* 3:447.

Osteosarcoma is an exceedingly malignant tumor that usually occurs in children and young adults. The type and extent of the tumor determines the type of treatment which ranges from variously-administered chemotherapeutic agents to limb amputation in conjunction with chemotherapy.

U.S. Pat. No. 4,621,077 discloses diphosphonic acids of general formula

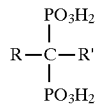

wherein R is fluorine or a linear or branched optionally substituted alkyl radical containing between 1 and 5 carbon atoms and R' is OH or fluorine. These compounds are useful in treating urolithiasis or as inhibitors of bone reabsorption.

U.S. Pat. No. 4,746,654 discloses methylene diphosphonic acid derivatives useful as anti-inflammatory agents.

Japanese published patent application 90-104593 discloses compounds of the formula $ACO[R(CH_2)_nCO]_m NHCH(PO_3H_2)_2$ wherein ACO is the residue of diclofenac or flufenamic acid, R=NH or O, m=0 or 1 and n=1–10.

U.S. Pat. No. 4,922,007 discloses an improved process for the preparation of 4-amino-1-hydroxybutane-1,1-disphosphonic acid.

French published patent application 2 683 527 discloses cortisone derivatives of gem-bisphonates.

French published patent application 2 683 528 discloses nonsteroidal antiinflammatory arylacetic and aryl proponic acid derivatives of gem-bisphonics.

French published patent application 2 683 529 discloses gem-diphosphonate analogs of cis-platinum.

U.S. Pat. No. 5,220,021 discloses geminal diphosphonate derivatives of an unsaturated 5-membered diheterocycloaliphatic ring useful as anti-arthritic agents.

U.S. Pat. No. 5,524,544 discloses methylene diphosphonic acid derivatives useful as inhibitors of cholesterol biosynthesis.

OBJECTS OF THE INVENTION

It is an object of the present invention to provide pharmaceutically active agents having utility for treating various diseases, especially bone diseases. Further objects are to provide new pharmaceutically active chemical entities for treating osteomyelitis, urinary catheter-related infections, infectious urinary calculi, periodontal disease and osteosarcoma, and to provide methods for employing these new pharmaceutically active chemical entities in treatment of disease. Another object is to provide novel intermediates for preparing these new chemical entities. Still another object is to provide methods for the preparation of the foregoing materials. These and other objects of the present invention will be apparent from the following description.

SUMMARY OF THE INVENTION

Novel chemotherapeutic agents having utility in treating infectious diseases such as osteomyelitis, periodontal disease, certain urinary tract infections, infectious urinary tract stones, and bone cancer are obtained by combining chemically a diphosphonate (also called bisphosphonate) or diphosphonate ester compound with a pharmaceutically active chemical entity effective against the foregoing diseases.

DETAILED DESCRIPTION

The novel pharmaceutically active therapeutic chemical agents of the present invention are diphosphonate (also called bisphosphonate) derivatives of therapeutic agents effective in treating infectious diseases such as osteomyelitis, periodontal disease, certain urinary tract infections, infectious urinary tract stones, and bone cancer. The diphosphonate groups cause the therapeutic agent to be attracted to, and to concentrate on, the surfaces of various salt crystals and the more complex forms of such crystals, such as hydroxyapatite, a major constituent of bone and the surface of dentition. Bacteria associated with these crystals are thereby exposed to an elevated concentration of the therapeutic agent, relative to the surrounding milieu. Organisms harbored in bone (osteomyelitis), at the gum-dentition interface (periodontal disease), on the surface of salt-encrusted indwelling urinary catheters and in infectious urinary calculi, are targeted by the therapeutic agents.

Because of the relative inaccessibility of micro-organisms in this protected environment, there is a dangerous tendency on the part of attending physicians to treat these infections through indiscriminate use of antibiotics. This often leads to the development of resistant forms, a frequent occurrence, for example, in urinary tract infections. When treated according to the present invention, however, not only are the free-floating, planktonic organisms neutralized by the therapeutic agents disclosed herein but, more importantly, the source of the infection, namely the sessile forms adhering to the catheter are attacked.

Chemotherapy of osteosarcoma is another area in which the therapeutic agents of the present invention provide a two-part therapeutic advantage over agents not containing diphosphonate groups. Diphosphonate derivatives of antineoplastic drugs like methotrexate and adriamycin concentrate in bone tissue, thereby allowing lower effective doses to be employed, thus attenuating their toxicity and reducing side effects.

Diphosphonic acid compounds useful as intermediates in the present invention have the general formula V'—R—Z' (1) wherein V' is halogen, preferably Cl, Br and I, OH, SH, NR'R", COOR', CO—X wherein X is halogen or azido, O—CO—X wherein X is halogen, O—CO—OR', CO—SR', S—CO—X, NR'—CO—X, NR'—NHR", NR'—CN, NR'—C(=NH)—NH—CN, or metal (covalently bound or ionic), for example, Li, Na or Mg, wherein R, R' and R" are independently hydrogen or an organic group and Z' is

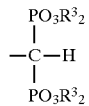

wherein each $R^3$ is independently H, alkyl or substituted alkyl of from 1 to about 10 carbons that may be linear or branched, saturated or unsaturated; cycloalkyl or substituted cycloalkyl of from 3 to about 10 carbons that may be saturated or unsaturated; monocyclic or polycyclic aryl such as, for example phenyl or naphthyl, optionally substitued by halogen, trifluoromethyl, alkyl of 1 to about 4 carbons, nitro, amino, hydroxy or carboxyl; aralkyl or substituted aralkyl, that is to say alkyl carrying an aryl substituent wherein the alkyl group has from 1 to about 10 carbons that may be linear or branched, saturated or unsaturated; or a saturated 5- or 6-membered heterocyclic such as, for example, piperidine, morpholine and piperazine, or 5- or 6-membered unsaturated heterocyclic such as, for example pyridine, furan, thiophene, pyrazine, pyrimidine, purine and imidazole.

Pharmaceutically active chemical entities useful in the present invention have the general formula A-V' wherein A is the residue of a pharmaceutically active chemical entity and V' has the meaning given above.

The compounds of the present invention have the general formula A—(V)$_m$—(R)$_n$—Z' (2) wherein m and n are independently 0 or 1, A, R, and Z' have the meanings given above and V is one of, but not limited to, O, S, NR', CONR', CO—O, O—CO, O—CO—O, CO—S, S—CO, S—CO—S, NR'—CO, O—CO—NR', NR'—CO—O, NR'—CO—NR", CO—NR'—NR", NR'—NR"—CO, NR'—C(=NH)—NR", NR'—C(=NH)—NH—C(=NH)—NR" or another acyclic or cyclic aliphatic or heteroorganic connecting structural unit; R, R', R", and Z' are as defined above, and R" is hydrogen or an organic group that can be the same as R' or can be different from R'. Compounds of the foregoing formula wherein either n or m is 1, or wherein both n and m are 1 are obtained by reacting various compounds of formula (1) with a pharmaceutically active chemical entity of formula A—V' carrying a functional group or substituent appropriate for the formation of the connecting structural unit by the chemical reaction.

Thus, when the pharmaceutically active chemical entity contains a halogen atom, it can be reacted with a diphosphonate compound of formula V'—R—Z' (1) wherein V' is primary or secondary amino to eliminate hydrogen halide and yield a compound of the formula A—NR'—R—Z' (3), which corresponds to formula (2) with n and m=1, and V=NR' wherein R' is H or an organic group such as alkyl or substituted alkyl; it can also be reacted with a reactant containing two primary or secondary amino groups in an acyclic or cyclic structure and with a compound of formula (1) wherein Y is halogen, to give a compound of formula (2) wherein n=1 and V is a connecting group attached by nitrogen atoms (—NR'—) to both A and R. Compounds of formula (3) can, however, be obtained as well by reacting a pharmaceutically active chemically entity compound containing a primary or secondary amino group with a compound of formula (1), respectively, containing a halogen atom.

Alternatively, when the pharmaceutically active chemical entity contains a carboxylic group, or a reactive carboxyl group derivative (e.g, acyl halide ester or azide), it can be reacted with a compound of formula (1) wherein V' is a primary or secondary amino group to eliminate water and form a compound of the formula A—CO—NR'—R—Z' (13), which corresponds to (2) with m=1, and n=1 and V=CONR', but also with a compound of formula (1) wherein V' can be, but is not limited to, for example, OH or SH, to give A—CO—V—R—Z' (14), respectively, wherein A, R and Z' have the previously stated meanings whereas V can be S, O or another atom or group which can connect CO to R by chemical bonds. Likewise, a compound of formula (1) wherein V' is COOH or a reactive derivative thereof (e.g, acyl halide, ester or azide) can be reacted with a pharmaceutically active chemical entity containing a primary or secondary amino group (A—NHR'), to give compounds of the formula A—NR'—CO—R—Z' (15) wherein A, R, and Z' have the previously stated meanings. The combination of groups, precursors, reactions and reaction conditions are easily understood by those skilled in the art in light of the discussions above. When one of the reactants or both contain other reactive groups than those needed to establish the chemical connection between A and R—Z', the interfering groups are protected by techniques established and known in the art.

In a particular embodiment, the group R in formula (2) can be $CH_2$, V is a nucleophilic atom or group Y, for example, a secondary amine or SH, or the entity W—Y wherein W is a group selected for its capacity to bond to the pharmaceutically active entity, and m=n=1. If the pharmaceutically active entity contains in itself a nucleophilic atom or group, a compound of the structure shown in the previous sentence with m=0 (A—$CH_2$—Z') is obtained. Examples of nucleophilic groups are secondary amine and SH.

Compounds of structure A—Y—$CH_2$—Z' (4) can be prepared by reacting a compound A—YH (5) with a tetraester of formula (6)

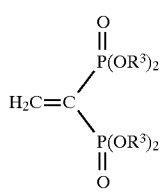

(6)

wherein $R^3$ has the same meaning as $R^3$ in the group Z' according to the procedure of D. W. Hutchinson & D. M. Thornton, *J. Orgmet. Chem.* 1988, 346, 341. The starting tetraesters can be prepared according to the procedures of C. R. Degenhardt and D. C. Burdsall, *J. Org. Chem.* 1986, 51, 3488–3490.

Compounds of the structure A—W—Y—CH$_2$—Z' (7) can be prepared by reacting a compound of formula W—YH (8) with a compound of formula (6) to form an intermediate of the formula W—Y—CH$_2$—Z' (9), and then reacting the intermediate with the pharmaceutically active entity A. Alternatively, reaction of the pharmaceutically active entity with a reagent W—YH (8) can be used to generate the intermediate A—W—YH, (10) which is then reacted with the tetraester of formula (6) as described in the previous paragraph. Examples of compounds W—YH are HO—CO—R—NHR', HOOC—R—SH and R'NH—R—NHR'.

Compounds of the structure A—CH2—Z' (11) can be prepared by reacting a pharmaceutically active entity containing a nucleophilic atom or group, represented by the formula AH (12), with a tetraester of the formula (6) as described previously.

Reaction of a compound of formula 6 with a secondary amine takes place in a polar solvent such as, for example, dichloromethane or chloroform at room temperature or at elevated temperatures of from about 20° C. to about 100° C. for a time of about two hours to about 72 hours. Preferably an amine, for example, triethylamine is present as a catalyst.

Diphosphonate esters of formulas (2), (3), (4), (7), (9), (11), (13), (14) and (15) can be converted to the corresponding gem-diphosphonic acids wherein R'=H by hydrolysis with aqueous HCl as described in U.S. Pat. No. 4,796,654. For sensitive compounds, which include most antibiotics, reaction with trimethylbromosilane in chloroform or CCl$_4$ is preferred, followed by reaction with water (no catalyst).

Pharmaceutically active chemical entities containing groups capable of reacting with the V'-substituent of the diphosphonates of formula (1), namely, carboxyl group or derivative thereof (e.g., acyl halide, ester, azide), primary and secondary amino group, hydroxyl, and halogen (Cl, Br and I) are useful according to the present invention. Consequently, examples of useful pharmaceutically active chemical entities include, without intending to be limiting thereto, aminoglycosides such as amikacin (U.S. Pat. No. 3,781, 268),
apramycin (U.S. Pat. No. 3,691,279), arbekacin (U.S. Pat. No. 4,107,424), bambermycin (U.S. Pat. No. 3,674, 866), butirosin (U.S. Pat. No. 3,541,078), dibekacin (German patent 2,135,191), dihydrostreptomycin (U.S. Pat. No. 2,498,574), fortimycin A (U.S. Pat. No. 3,976, 768) and fortimycin B (Japan Kokai 75 145,588), gentamicin (U.S. Pat. Nos. 3,091,572 and 3,136,704), isepamicin (Belgian patent 818,431), kanamycin (U.S. Pat. No. 2,931,798), micronomicin (German patent 2,326,781), neomycin (2,799,620),
neomycin undecylenate (US patent 3,022,286), n e t i l m i c i n (German patent 2,437,160), paromomycin (U.S. Pat. No. 2,916,485), ribostamycin (German patent 1,814,735), sisomicin (U.S. Pat. No. 3,832,286), spectinomycin (U.S. Pat. No. 3,234,092), streptomycin (U.S. Pat. No. 2,868,779), streptonicozid (Pennington et al., *J. Am. Chem. Soc.* 75, 2261 (1953) and tobramycin (Stark et al., Higgens,
Kastner; Thompson, Presti; Wick, Welles, *Antimicrob. Ag. Chemother.*, 1967, 314–348;

amphenicols such as azidamfenicol (U.S. Pat. No. 2,882, 275), chlorampphenicol [Bartz, *J. Biol. Chem.* 172, 445 (1948)], chloramphenicol palmitate (U.S. Pat. No. 2,662, 906), chloramphenicol pantothenate (U.S. Pat. No. 3,078, 300), florfenicol (U.S. Pat.No. 4,235,892) and thiamphenicol [Cutler et al., *J. Am. Chem. Soc.* 74, .5475 (1952)];

ansamycins such as rifamide (U.S. Pat. No. 3,313,804);

carbapenems, for example, imipenem (U.S. Pat. No. 4,194, 047);

cephalosporins, for example, cefaclor (U.S. Pat. No. 3,925, 372), cephadroxil U.S. Pat. No. 3,816,253), cefamandole U.S. Pat. No. 3,641,021), cefatrizine (U.S. Pat. No. 3,970, 651), cefazedone (German patent 2,345,402), cefazolin (U.S. Pat. No. 3,516,997), cefixime (U.S. Pat. No. 4,409, 214), cefmenoxime (U.S. Pat. No. 4,098,888), cefodizime (U.S. Pat. No. 4,278,793), cefonicid (U.S. Pat. No. 4,093, 723), cefoperazone (U.S. Pat. No. 4,410,5220, ceforanide (U.S. Pat. No. 4,172,196), cefotaxime (U.S. Pat. No. 4,098, 888), cefotiam (German patent 2,607,064), cefpimizole (U.S. Pat. No. 4,217,450), cefpiramide (Belgian patent 833, 063), cefpodoxime proxetil (U.S. Pat. No. 4,486,425), cefroxidine (U.S. Pat. No. 4,073,902), cefsulidin, (U.S. Pat. No. 4,065,619), ceftazidime (U.S. Pat. No. 4,258,041), cefteram (Belgian patent 890,499), ceftozole (U.S. Pat. No. 3,516,997), ceftibuten (U.S. Pat. No. 4,634,697), ceftizoxime (U.S. Pat. No. 4,427,674), ceftriaxone (U.S. Pat. No. 4,327,210), cefuroxime (U.S. Pat. No. 3,974,153), cefuzonam (U.S. Pat. No. 4,399,132), cephalexin (U.S. Pat. No. 3,275,626), cephaloglycin (U.S. Pat. No. 3,422,103), cephaloridine (French patent 1,384,197), cephalosporin C (U.S. Pat. No. 3,082,155), cephalothin (French patent 1,384,197), cephapirin sodium (U.S. Pat. No. 3,422,100), cephradine (U.S. Pat. No. 3,485,819) and pivecfalexin (German patent 1,951,012);

cephamycins such as cefbuperazone (U.S. Pat. No. 4,263, 292), cefmetazole (U.S. Pat. No. 4,007,177), cefminox (U.S. Pat. No. 4,357,331), cefotetan (U.S. Pat. No. 4,263,432) and cefoxitin (U.S. Pat. No. 4,297,488);

monobactams such as aztreonam (Netherlands patent application 8,100,571, carumonam (U.S. Pat. No. 4,572,801), and tigemonam (U.S. Pat. No. 4,638,061);

oxacephems such as flomoxef (U.S. Pat. No. 4,532,233) and moxalactam (U.S. Pat. No. 4,138,486);

penicillins such as amdinocillin (U.S. Pat. No. 3,957,764, amoxicillin (U.S. Pat. No. 3,192,198) ampicillin (U.S. Pat. No. 2,985,648), carbenicillin (U.S. Pat. No. 3,142,673), clometocillin (U.S. Pat. No. 3,007,920), cloxacillin (Doyle et al., *J. Chem. Soc.* 1963, 5838), cyclacillin (U.S. Pat. No. 3,194,802), dicloxacillin (U.S. Pat. No. 3,239,507), epicillin (U.S. Pat. No. 3,485,819), floxacillin (U.S. Pat. No. 3,239, 507), hetacillin (U.S. Pat. No. 3,198,804), lenampicillin (U.S. Pat. No. 4,342,693), metampicillin (Belgian patent 661,232), oxacillin (U.S. Pat. No. 2,996,501), penicillin V (Brandl et al., *Wien. Med. Wochenschr.* 1953, 602), piperacillin (U.S. Pat. No. 4,087,424), pivampicillin ((U.S. Pat. No. 3,660,575), propicillin (British patent 877,120), sulbenicillin (U.S. Pat. No. 3,660,379) and ticarcillin (U.S. Pat. No. 3,282,926);

lincosamides such as clindamycin (U.S. Pat. No. 3,475,407) and lincomycin (U.S. Pat. Nos. 3,086,912 and 3,155,580);

macrolides such as azithromycin (U.S. Pat. No. 4,517,359), carbomycin (U.S. Pat. No. 2,960,438), clarithromycin (U.S. Pat. No. 4,331.803), erythromycin (U.S. Pat. No. 2,823, 203), josamycin (Japanese patent 66 21,759), leucomycins (U.S. Pat. No. 3,535,309), midecamycins (U.S. Pat. No. 3,761,588), miokamycin (Japanese Kokai 74 124087), oleandomycin (U.S. Pat. Nos. 2,757,123 and 2,842,481), primycin (U.S. Pat. No. 3,498,884), rokitamycin (German patent 2,918,954), rosaramicin (S. African patent 71 00,402), roxithromycin (U.S. Pat. No. 4,359,545), spiramycin (U.S. Pat. No. 2,943,023), and troleandomycin (British patent 877,730);

polypeptides such as bacitracin (U.S. Pat. No. 2,915,432), capreomycin (U.S. Pat. No. 3,143,468), colistin (Japanese patent 57 4898), enduracidin (British patent 1,163,270), enviomycin (U.S. Pat. No. 3,892,732), gramicidin (U.S. Pat. No. 2,534,541), mikamycin (French patent 1,349,946), polymyxin (U.S. Pat. No. 2,565,057), polymyxin B-methanesulfonic acid (U.S. Pat. No. 3,044,934), pristinamycin (U.S. Pat. No. 3,154,475), ristocetin (U.S. Pat. No. 2,990,329), Teicoplanin (U.S. Pat. No. 4,239,751), thiostrepton (U.S. Pat. Nos. 2,982,689 and 2,982,698), tuberactinomycin (U.S. Pat. No. 3,639,580), tyrocidine (U.S. Pat. No. 3,265,572), tyrothricin, vancomycin (U.S. Pat. No. 3,067,099), viomycin (U.S. Pat. No. 2,633,445), virginiamycin, and zinc bacitracin (U.S. Pat. No. 2,803, 584);

tetracyclines such as apicycline (Netherlands patent application 6,515,688), chlortetracycline (U.S. Pat. No. 2,482, 055), clomocycline (Belgian patent 628,142), demeclocycline (U.S. Pat. No. 2,878,289), doxycycline (U.S. Pat. No. 3,200,149), guamecycline (British patent 1,042,207), lymecycline (U.S. Pat. No. 3,043,716), meclocycline U.S. Pat. No. 2,984,686), methacycline (U.S. Pat. No. 3,026,354), minocycline (U.S. Pat. Nos. 3,148,212 and 3,226,436), oxytetracycline (U.S. Pat. No. 2,516,080), penimepicycline (British patent 897,826), pipacycline (British patent 888, 968), rolitetracycline (U.S. Pat. No. 3,104,240), sancycline (U.S. Pat. No. 3,019,260), senociclin (U.S. Pat. No. 3,218, 335), and tetracycline (U.S. Pat. No. 2,699,054);

cycloserine (U.S. Pat. No. 2,773,878), doxorubicin (U.S. Pat. No. 3,590,028), and mupirocin (U.S. Pat. No. 3,977, 943);

2,4-diaminopyrimidines such as brodimoprim (U.S. Pat. No. 4,024,145), tetroxoprim (U.S. Pat. No. 3,992,379), and trimethoprim (U.S. Pat. No. 3,049,544);

nitrofurans such as furazolium chloride (U.S. Pat. No. 3,169,970), nifuradene (U.S. Pat. No. 2,746,960), nifurprazine (British patent 966,832), nifurtoinol (U.S. Pat. No. 3,446,802), and nitrofurantoin (U.S. Pat. No. 2,610,181);

quinolones and analogs such as amifloxacin (U.S. Pat. No. 4,499,091), cinoxacin (U.S. Pat. No. 3,669,965), ciprofloxacin (U.S. Pat. No. 4,670,444), difloxacin (U.S. Pat. No. 4,730,000), enoxacin (U.S. Pat. No. 4,359,578), fleroxacin (U.S. Pat. No. 4,398,029), flumequine (U.S. Pat. No. 3,896, 131), lomefloxacin (U.S. Pat. No. 4,528,287), miloxacin (U.S. Pat. No. 3,799,930), nalidixic acid (U.S. Pat. No. 3,149,104), norfloxacin (U.S. Pat. No. 4,146,719), ofloxacin (U.S. Pat. No. 4,382,892), oxolinic acid (U.S. Pat. No. 3,287,458), pefloxacin (U.S. Pat. No. 4,292,317), pipemidic acid (U.S. Pat. No. 3,887,557), piromidic acid (British patent 1,129,358), rosoxacin (U.S. Pat. No. 3,753,993), sparfloxacin (*Antimicrobial Agents & Chemotherapy* 1989, 33, 1167–1173) and tosufloxacin (U.S. Pat. No. 4,704,459);

sulfonamides such as acetyl sulfamethoxypyrazine (U.S. Pat. No. 3,098,069), acetyl sulfisoxazole (U.S. Pat. No. 2,721,200), azosulfamide ( U.S. Pat. Nos. 2,123,634 and 2,148,910), benzylsulfamide, chloramine-B, chloramine-T, dichloramine T (U.S. Pat. No. 2,495,489), formosulfathizale [Druey et al., *Heav. Chim. Acta* 31, 2184 (1948)], $N^2$-formylsulfisomidine (German patents 1,122,511 and 1,126,857), $N^4$-β-D-glucosylsulfanilamide [Kuhn et al., *Ber.* 71, 621 (1938)], mafenide (U.S. Pat. No. 2,288,531), 4'-(methylsulfamoyl)sulfan-ilanilide (French patent 817,034), p-nitrosulfathiazole (U.S. Pat. No. 2,443,742), norprylsulfamide (U.S. Pat. No. 2,262,544), phthalylsulfacetamide [(Basu, *J. Indian Chem. Soc.* 26, 130 (1949)], phthalylsulfathiazole (U.S. Pat. Nos. 2,324,013 and 2,324,015), salazosulfadimidine [Korkuczanski, *Przem. Chem.* 37, 162 (1958)], succinylsulfathiazole ( U.S. Pat. Nos. 2,324,013 and 2,324,014), sulfabenzamide (U.S. Pat. No. 2,240,496), sulfacetamide (U.S. Pat. No. 2,411,495, sulfachlorpyridazine (U.S. Pat. No. 2,790,798), sulfachrysoidine [Gley et al., *Compt. Rend. Soc. Biol.* 125, 1027 (1937)], sulfacytine (U.S. Pat. No. 3,375,247), sulfadiazine ( U.S. Pat. No. 2,407,966), sulfadicramide (U.S. Pat. No. 2,417,005), sulfadimethoxine (U.S. Pat. No. 2,703,800), sulfadoxine (U.S. Pat. No. 3,132,139), sulfaethidole [Wojahn et al., *Arch. Pharm.,* 284, 53 (1951)], sulfaguanidine (U.S. Pat. Nos. 2,218,490, 2,229,784 and 2,233,569), sulfaguanole (U.S. Pat. No. 3,562,258), sulfalene (U.S. Pat. No. 3,098,069), sulfaloxic acid (German patent 960,190), sulfamerazine (U.S. Pat. No. 2,407,966), sulfameter (U.S. Pat. No. 3,214, 335), sulfamethazine (U.S. Pat. No. 2,407,966), sulfamethizole (U.S. Pat. No. 2,447,702), sulfamethomidine (German patent 926,131), sulfamethoxazole (U.S. Pat. No. 2,888,455), sulfamethoxypyridazine (U.S. Pat. No. 2,712, 012), sulfametrole (U.S. Pat. No. 3,247,193), and sulfamidochrysoidine (U.S. Pat. No. 2,085,037);

sulfones such as acedapsone [Fromm et al., *Ber,* 41, 2270 (1908)], acediasulfone [Jackson, *J. Am. Chem. Soc.* 70, 680 (1948)], acetosulfone sodium (U.S. Pat. No. 2,358,365), dapsone (French patent 829,926), diathymosulfone (British patent 758,744), glucosulfone sodium (Swiss patent 234, 108), solasulfone (British patent 491,265), succisulfone (U.S. Pat. No. 2,268,754), sulfonilic acid, p-sulfanilylbenzylamine (Dewing,*J. Chem. Soc.* 1946, 466), p,p'-sulfonyldianiline-N,N'-digalactoside, sulfoxone sodium (U.S. Pat. No. 2,256,575), and thiazolsulfone (2,389,126);

others such as clofoctol (U.S. Pat. No. 3,830,852), hexedine (U.S. Pat. No. 3,357,886), nitroxoline [Kostanecki, *Ber.* 24, 154 1891)], xibornol (British patent 1,206,774); hydnocarpic acid [Diaper et al., Biochem J. 42, 581 (1948)], p-amino-salicylic acid (U.S. Pat. No. 427,564), p-aminosalicylic acid hydrazide (Spanish patent 206,645), benzoylpas (British patent 676,363), 5-bromosalicylhydroxamic acid (Urbanski et al., *Nature* 170, 753 (1952), capreomycin (U.S. Pat. No. 3,143,468), clofazimine (Barry et al., *Nature* 179, 1013 (1957), cyacetacide (U.S. Pat. No. 2,849,369), dihydrostreptomycin (U.S. Pat. No. 2,498,574), enviomycin (U.S. Pat. No. 3,892,732), ethambutol [Wilkinson et al., *J. Am. Chem. Soc.* 83, 2212 (1961)], ethionamide (British patent 800,250), 4'-formylsuccinanilic acid (German patent 852,086), furonazide [Miyatake et al. *J. Pharm. Soc. Japan* 75, 1066, (1955)], glyconiazide (U.S. Pat. No. 2,940,899), isobutol (U.S. Pat. No. 3,718,655), isonizid (U.S. Pat. No. 2,830, 994), isoniazid methanesulfonate (U.S. Pat. No. 2,759,944), morphazinzmide (German patent 1,129,492), opiniazide [Pershin et al., *C.A.* 51, 10747e (1957)], pasiniazide (Swiss patent 303,085), phenyl aminosalicylate (U.S. Pat. No. 2,604,488), protionamide (British patent 800,250), pyrazinamide (German patent 632,257), rifampin (U.S. Pat. No. 3,342,810), salinizid [Hart et al., *Antibot. & Chemother.* 4, 803 (1954)], subathizone [Bernstein et al., *J. Am. Chem. Soc.* 73, 906 (1951), sulfoniazide (U.S. Pat. No. 2,727,041), thiacetazone [Domagk et al., *Naturwiss* 33, 315 (1946)], tiocarlide (U.S. Pat. No. 2,703,815), tuberactinomycin (U.S. Pat. No. 3,639,580), tubercidin [Anzai et al., *J. Antiobiot.* 1OA, 201 (1957)], tuberin (Japanese patent 64 7399), verazide [Fox et al., *J. Org. Chem.* 18, 983 (1953), viomycin (U.S. Pat. No. 2,633,445), and viomycin pantothenate (German patents 954,874 and 1,011,800).

The compounds of the present invention are intended for treatment of a member of a mammalian species, e.g., dogs, mice, primates and humans, and normally are administered orally but also can be administered by injection. For oral administration, the compounds can be used at a dosage amount that, in general, is less than that at which the pharmaceutically active component itself is employed. The compounds of the present invention are used in the form of various pharmaceutical preparations such as tablets, capsules, powders, granules, syrups and the like which are well known in the art, and which can be prepared by methods known per se using suitable diluents, bindings, disintegrators, coating agents and the like. Other preparations suitable for injection can also be prepared by techniques known in the art.

The following examples illustrate the present invention without, however, limiting the same thereto.

EXAMPLE 1

6-Fluoro-1-ethyl-7-{4-[2,2-bis(diethoxyphosphono)-1-ethyl]-1-piperazyl}-4-oxo-1,4-dihydroquinoline-3-carboxylic acid To a stirred solution of 1.0 g (3.33 mmol) of tetraethyl ethenylidenediphosphonate (prepared according to the procedure of Degenhardt et al., *J. Org. Chem.* 1986 51, 3488) and triethylamine (0.8 ml, 5.7 mmol) in dry dichloromethane (10 ml), norfloxacin (0.64 g, 2.0 mmol) was added and the mixture was agitated for 16 hours at room temperature. The homogeneous reaction mixture was evaporated to dryness and the residue was triturated with anhydrous ether to give 1.2 g (73% yield) of crystalline product, mp 196°–197° C.

The antibacterial action of the product was evaluated against the following bacterial strains:

Gram positive bacteria: *Staphylococcus aureus* ATCC 25923

*Staphylococcus epidermidis* OKI 110001
*Streptococcus faecalis* OKI 80171
Gram negative bacteria: *Salmonella typhi* OKI 10084
*Escherichia coli* OKI 35034
*Proteus vulgaris* OKI 60002
*Pseudomonas aeruginosa* ATCC 27853

The sensitivity of the foregoing bacterial strains to both the product of Example 1 and norfloxacin was investigated by the broth-dilution method, and the minimal inhibitory concentration (MIC) values were assessed. MIC was defined as the lowest concentration ( g/ml) at which no bacterial growth could be observed visually.

The antibiotics were dissolved in dimethylsulfoxide (DMSO) and the solution was diluted by nine consecutive 2-fold dilutions in Nutrient-broth (NB) culture medium. Aliquots (0.2 ml) from each of these diluted solutions were added to test tubes containing 1.6 ml NB culture medium. The antibiotics were investigated in the concentration range of 100–0.38 µg/ml.

After overnight culture in NB at 37° C., the bacterial cultures were diluted so that their optical densities (OD) at 620 nm were between 0.08–0.1. As these bacterial suspensions had $10^7$ colony forming units per ml (CFU/ml), they were further diluted in NB culture medium so that the inoculated test tubes had a final concentration of $10^{5-6}$ CFU/ml and a final volume of 2 ml. Such CFU count did not result in turbidity.

Incubation of the test tubes took place in a thermostat at 37° C. The test tubes were inspected visually after 24 and 48 hours. The margin of error of in vitro sensitivity determination was ± one dilution step. MIC values were read after 48 hours of incubation. The MIC value was the lowest antibiotic concentration at which no bacterial growth was observed, i.e. the culture medium remained clear. The MIC values in the following table represent the arithmetic mean of three independent experiments.

| BACTERIA | NORFLOXACIN MIC (µg/ml) | COMPOUND OF EX. 1 MIC (µg/ml) |
|---|---|---|
| *Staphylococcus aureus* ATCC 25923 | 6.25 | 12.5 |
| *Staphylococcus epidermidis** OKI 110001 | 6.25 | 12.5 |
| *Streptococcus faecalis* OKI 80171 | 12.5 | 12.5 |
| *Salmonella typhi* OKI 10084 | 12.5 | 25 |
| *Escheria coli* OKI 35034 | 6.25 | 25 |
| *Proteus vulgaris* OKI 60002 | 6.25 | 3.12 |
| *Pseudomonas aeruginosa* ATCC 27853 | 25 | 50 |

* = only two experiments

EXAMPLE 2

9-Fluoro-3-methyl-10-{4-[4,4-bis(diethoxyphosphono)-butyl3-1-piperazyl}-7-oxo-2,3-dihydro-7H-pyrido[1,2,3-de][1,4]benzoxazine-6-carboxylic acid The sodium salt of tetraethyl methylenebisphosphonate is prepared as described in *J. Am. Chem, Soc.* 1962, 84, 4454, and reacted with 1-bromo-3-chloropropane by the procedure in *J. Am. Chem. Soc.* 1953, 75, 1500, to give tetraethyl 4-chloro-1,1-butanediphosphonate. Reaction with piperazine yields tetraethyl 4-(1-piperazyl)-1,1-butanediphosphonate. 9,10-Difluoro-3-methyl-7-oxo-2,3-dihydro-7H-pyrido[1,2,3-de][1,4]benzoxazine-6-carboxylic acid is prepared following the procedure of example 2 of U.S. Pat. No. 4,382,892. This acid is then subjected to the procedure of example 3 of the same patent, except substituting for N-methylpiperazine an equivalent amount of tetraethyl 4-(1-piperazyl)-1,1-butane diphosphonate. The crude product gives after extraction, solvent evaporation and recrystallization 9-fluoro-3-methyl-10-{4-[4,4-bis(diethoxyphosphono)-butyl]-1-piperazyl}-7-oxo-2, 3-dihydro-7H-pyrido[1,2,3-de][1,4]-benzoxazine-6-carboxylic acid.

EXAMPLE 3

9-Fluoro-3-methyl-10-{4-[3,3-bis(diethoxyphosphono)-1-propyl]-1-piperazyl}-7-oxo-2,3-dihydro-7H-pyrido[1,2,3-de][1,4]benzoxazine-6-carboxylic acid The procedure of Example 2 is used, replacing 1-bromo-3-chloropropane by 1-bromo-2-chloroethane, to give as intermediates first tetraethyl 3-chloro-1,1-propanediphosphonate and then (by reaction with piperazine) tetraethyl 3-(1-piperazyl)-1,1-propanediphosphonate. Reaction of the latter with 9,10- difluoro-3-methyl-7-oxo-2,3-dihydro-7H-pyrido [1,2,3-de][1,4]benzoxazine-6-carboxylic acid yields 9-fluoro-3-methyl-10-{4-[3,3-bis (diethoxyphosphono)-1-propyl}-1-piperazyl}-7-oxo-2,3-dihydro-7H-pyrido [1,2,3-de][1,4]benzoxazine-6-carboxylic acid.

EXAMPLE 4

9-Chloro-3-methyl-10-{4-[2,2-bis(diethoxyphosphono)-1-ethyl]-l-piperazyl}-7-oxo-2,3-dihydro-7H-pyrido[1,2,3-de][1,4]benzoxazine-6-carboxylic acid Reaction of piperazine with tetraethyl ethenylidenebisphosphonate according to the procedure described in Example 1, above, gives tetraethyl 2-(1-piperazyl)-1,1-ethanediphosphonate. Reaction of the latter with 9-chloro-10-fluoro-3-methyl-7-oxo-2,3-dihydro-7H-pyrido[1,2,3-de][1,4]benz-oxazine-6-carboxylic acid yields the title compound.

EXAMPLE 5

9-Fluoro-3-methyl-10-{4-[2,2-bis(diethoxyphosphono)-1-ethyl]-1-piperazyl}-7-oxo-2,3-dihydro-7H-pyrido[1,2,3-de][1,4]benzoxazine-6-carboxylic acid The procedure of example 3 of U.S. Pat. No. 4,382,892 is repeated, except substituting for N-methylpiperazine an equivalent amount of tetraethyl 2-(1-piperazyl)-1,1-ethanediphosphonate prepared as described in example 4 above, to yield the title compound.

EXAMPLE 6

6-Chloro-1-ethyl-7-{4-[3,3-bis(diethoxyphosphono)-1-propyl]-1-piperazyl}-4-oxo-1,4-dihydroquinoline-3-carboxylic acid 6, 7-Dichloro-1-ethyl-4-oxo-1 ,4-dihydroquino line-3-carboxylic acid is prepared according to the procedure of U.S. Pat. No. 4,292,317. The acid is then employed in the procedure of Example 31 of the cited patent except substituting for 1-methyl hydrazine an equivalent amount of tetraethyl 3-(1-piperazyl)-1,1-propanediphosphate to yield 6-chloro-1-ethyl-7-{4-[3,3-bis (diethoxyphosphono)-1-propyl]-1-piperazyl}-4-oxo-1,4-dihydroquinoline-3-carboxylic acid.

For oral administration, suitable forms of administration are, for example, compressed tablets, capsules, pills and suspensions. The solid forms preferably contain at least 100 mg of 6-chloro-1-ethyl-7-{4-[3,3-bis(diethoxy-phosphono)-1-propyl]-1-piperazyl]-4-oxo-1,4-dihydroquinoline-3-carboxylicacid. Suitable carriers for such solid forms are, for example, lactose, starch, talc, gelatin and magnesium stearate. Aqueous forms preferably contain at least 20 mg of the active compound per ml. Water soluble high molecular weight compounds such as, for example, cellulose esters and polyethylene glycols, may be included in such suspensions as stabilizers. Sweetening agents, aromatising agents and/or colorants also may be added.

EXAMPLE 7

6-Fluoro-1-(3,3-diphosphono-1-propyl)-7-(4-methyl-1-piperazyl)-4-oxo-1,4-dihydroquinoline-3-carboxylic acid 7-Chloro-3-ethoxycarbonyl-6-fluoro-4-oxo-1,4-dihydroquinoline is reacted with Cl-(CH$_2$)$_2$-Z' (tetraethyl 3-chloro-1,1-propanediphosphonate) and gives 1-[3,3-bis (diethoxyphosphono)-1-propyl]-3-ethoxycarbonyl-6-fluoro-4-oxo-1,4-dihydroquinoline which, in turn, is treated with 1-methylpiperazine to yield 1-[3,3-bis(diethoxyphosphono)-1-propyl]-3-ethoxycarbonyl-6-fluoro-7-(4-methyl-1-piperazyl)-4-oxo-1,4-dihydroquinoline. This product is saponified according to the procedure of example 20 of the cited patent to give the title compound.

EXAMPLE 8

1-Cyclopropyl-7-{4-[3,3-bis(diethoxyphosphono)-1-propyl]-1-piperazyl}-4-oxo-1,4-dihydro-1,6-naphthyridine-3-carboxylic acid 7-Chloro-1-cyclopropyl-4-oxo-1,4-dihydro-1,6-naphthyridine-3-carboxylic acid is prepared following the procedure of example 20(e) of U.S. Pat. No. 4,670,444. The acid is then employed in the procedure of the cited patent except substituting for N-methylpiperazine an equivalent amount of tetraethyl 3-(1-piperazyl)-1,1-propanediphosphonate to yield 1-cyclopropyl-7-{4-[3,3-bis (diethoxyphosphono)-1-propyl]-1-piperazyl}-4-oxo=1,4-dihydro-1,6-naphthyridine-3-carboxylic acid.

A tablet formulation is prepared from the following formulation:

| | |
|---|---|
| 1-cyclopropyl-7-{4-(3,3-bis(di-ethoxyphosphono)-1-propyl)-1-piperazyl}-4-oxo-1,4-dihydro-1,6-naphthyridine-3-carboxylic acid | 290.0 mg |
| Avicel | 47.0 mg |
| Moist corn starch | 13.5 mg |
| Pregelatinized starch | 6.0 mg |
| Magnesium stearate | 3.5 mg |
| Film coating | |
| HPM cellulose | 3.0 mg |
| Polyethylene glycol 4000 | 1.0 mg |
| Titanium dioxide | 1.0 mg |

EXAMPLE 9

7-(4-Methylpiperazino)-1-cyclopropyl-3-{[2,2-bis (diethoxyphosphono)-1-oxo]-1-ethyl}-4-oxo-1,4-dihydro-1,6-naphthyridine 7-(4-Methylpiperazino)-1-cyclopropyl-4-oxo-1,4-dihydro-1,6-naphthyridine-3-carboxylic acid, which is prepared as described in U.S. Pat. No. 4,670,444, is converted to its acid chloride and reacted with the sodium salt of tetraethyl methylenebisphosphonate prepared as quoted in Example 2, above, to give after product purification 7-(4-methylpiperazino)-1-cyclopropyl-3-{[2,2-bis (diethoxyphosphono)-1-oxo]-1-ethyl}-4-oxo-1,4-dihydro-1,6-naphthyridine.

EXAMPLE 10

1-Cyclopropyl-6-fluoro-7-{4-[3,3-bis (diethoxyphosphono)-1-propyl]-1-piperazyl}-4-oxo-1,4-dihydroquinoline-3-carboxylic acid 7-Chloro-1-cyclopropyl-6-fluoro-1,4-dihydro-4-oxo-quinoline-3-carboxylic acid is prepared according to the procedure described in column 7–8 of U.S. Pat. No. 4,670, 444. The acid is then employed in the procedure of example 23 of the cited patent except substituting for piperazine an equivalent amount of tetraethyl 3-(1-piperazyl)-1,1-propanediphosphonate to yield 1-cyclopropyl-6-fluoro-7-{4-[3,3-bis(diethoxyphosphono)-1-propyl]-1-piperazyl}-4-oxo-1,4-dihydroquinoline-3-carboxylic acid.

EXAMPLE 11

1-Cyclopropyl-6-fluoro-7-{4-[2,2-bis (diethoxyphosphono)-1-ethyl]-1-piperazyl}-4-oxo-1,4-dihydroquinoline-3-carboxylic acid 1-Cyclopropyl-6-fluoro-7-(1-piperazyl)-4-oxo-1,4-dihydroquinoline-3-carboxylic acid is prepared according to the procedure of example 23 of U.S. Pat. No. 4,670,444 and is reacted with tetraethyl ethenylidenebisphosphonate as described in Example 1, above, to yield 1-cyclopropyl-6-fluoro-7-{4-[2,2-bis (diethoxyphosphono)-1-ethyl]-1-piperazyl}-4-oxo-1,4-dihydro-quinoline-3-carboxylic acid.

EXAMPLE 12

6-{2-Ethoxy-5-[3,3-bis(diethoxyphosphono)-1-propylamino]-naphth-1-oyl}-amino-3,3-dimethyl-7-oxo-4-thia-1-azabicyclo [3.2.0]heptane-2-carboxylic acid and isomers 5-Amino-2-ethoxy-1-naphthoic acid is converted to its salt and then is reacted with tetraethyl 3-chloro-1,1-propanediphosphonate in the presence of sodium carbonate. Isolation and purification yield 2-ethoxy-5-[3,3-bis (diethoxyphosphono)-1-propylamino]-1-naphthoicacid. The latter is condensed by the procedure disclosed in U.S. Pat. No. 3,132,136 with aminopenicillanate to afford 6-{2-ethoxy-5-[3,3-bis (diethoxyphosphono)-1-propylamino]-1-naphthoyl}-amino-3,3-dimethyl-7-oxo-4-thia-1-azabicyclo [3.2.0]heptane-2-carboxylic acid.

Substituting 3-amino-2-ethoxy-1-naphthoic acid for 5-amino-2-ethoxy-1-naphthoic acid in the foregoing procedure yields 6-{2-ethoxy-3-[3,3-bis(diethoxyphosphono)-1-propylamino]-1-naphthoyl}-amino-3,3-dimethyl-7-oxo-4-thia-1-azabicyclo [3.2.0]heptane-2-carboxylic acid.

Substituting 4-amino-2-ethoxy-1-naphthoic acid for 5-amino-2-ethoxy-1-naphthoic acid in the foregoing procedure yields 6-{2-ethoxy-4-(3,3-bis(diethoxyphosphono)-1-propylamino1-1-naphthoyl3-amino-3,3-dimethyl-7-oxo-4-thia-1-azabicyclo [3.2.0]heptane-2-carboxylic acid.

Substituting 6-amino-2-ethoxy-1-naphthoic acid for 5-amino-2-ethoxy-1-naphthoic acid in the foregoing procedure yields 6-{2-ethoxy-6-[3,3-bis(diethoxyphosphono)-1-propylamino]-1-naphthoyl}-amino-3,3-dimethyl-7-oxo-4-thia-1-azabicyclo [3.2.0]heptane-2-carboxylic acid.

Substituting 7-amino-2-ethoxy-1-naphthoic acid for 5-amino-2-ethoxy-1-naphthoic acid in the foregoing procedure yields 6-{2-ethoxy-7-(3,3-bis(diethoxyphosphono)-1-propylamino]-1-naphthoyl}-amino-3,3-dimethyl-7-oxo-4-thia-1-azabicyclo [3.2.0]heptane-2-carboxylic acid.

EXAMPLE 13

6-[3,3-bis(diethoxyphosphono)-propanoyl]amino-3,3-dimethyl-7-oxo-4-thia-1-azabicyclo [3.2.0]heptane-2-carboxvlic acid 3,3-Bis(diethoxyphosphono)-propanoic acid is prepared according to Dutch patent application 6,514,133 and is reacted with benzhydryl aminopenicillanate to give 6-[3,3-bis(diethoxy-phosphono)-propanoyl]amino-3,3-dimethyl-7-oxo-4-thia-1-azabicyclo [3.2.0]heptane-2-carboxylic acid benzhydryl ester. Cleavage of the benzhydryl ester group with trifluoric acid and anisole gives the title compound.

EXAMPLE 14

7β-[α-(Z-Methoxyimino)-α-(2-aminothiazol-4-yl)-acetamido]-3-[3,3-bis (diethoxyphosphono)-propanoyloxymethyl]-3-cephem-4-carboxylic acid 3,3-Bis(diethoxyphosphono)-propanoic acid is converted to its acid chloride by reaction with oxaloyl chloride. The reaction of benzhydryl 7β-{α-(Z-methoxyimino)-α-[2-(tert-butoxycarbonylamino-)thiazol-4-yl]-acetamido}-3-hydroxymethyl-3-cephem-4-carboxylate with the 3,3-bis (diethoxyphosphono)-propanoyl chloride in the presence of pyridine leads to benzhydryl 7β-{α-(Z-methoxyimino)-α-[2-( tert-butoxycarbonylamino-)thiazol-4-yl]-acetamido}-3-[3,3-bis(diethoxyphosphono)-propanoyloxy-methyl]-3-cephem-4-carboxylate. Deprotection with cold trifluoric acid and anisole yields 7β-[α-(Z-methoxyimino)-α-(2-aminothiazol-4-yl)-acetamido]-3-[3,3-bis (diethoxyphosphono)-propanoyloxy-methyl]-3-cephem-4-carboxylic acid.

EXAMPLE 15

7β-{α-(Z-Methoxyimino)-α-[2-(3,3-bis(diethoxyphosphono)-1-propylamino)-thiazol-4-yl]-acetamido}-3-acetoxymethyl-3-cephem-4-carboxylic acid Reaction of Cl-(CH₂)₂-Z'(tetraethyl 3-chloro-1,1-propanediphosphonate) with 7β-[α-(Z-methoxyimino)-α-(2-aminothiazol-4-yl)-acetamidol-3-hydroxymethyl-3-cephem-4-carboxylic acid in the presence of sodium carbonate yields the title compound.

EXAMPLE 16

7β-{α-(Z-Methoxyimino)-α-[2-(3,3-bis(diethoxyphosphono)-propanoylamino)-thiazol-4-yl]-acetamido}-3-acetoxymethyl-3-cephem-4-carboxylic acid 3,3-Bis(diethoxyphosphono)-propanoyl chloride is prepared as in Example 14 and is reacted with 7β-[α-(Z-methoxyimino)-α-(2-aminothiazol-4-yl)-acetamido]-3-acetoxymethyl-3-cephem-4-carboxylic acid in the presence of pyridine and forms 7β-{α-(Z-methoxyimino)-α-[2-(3,3-bis(diethoxyphosphono)-propanoylamino)-thiazol-4-yl]-acetamido}-3-acetoxymethyl-3-cephem-4-carboxylic acid.

EXAMPLE 17

7β-[3,3-Bis(diethoxyphosphono)-propanoylamino]-7-methoxy-3-carbamoyloxymethyl-3-cephem-4-carboxylic acid Bis(diethoxyphosphono)-propanoyl chloride, preparedas in Example 14, is reacted with 7β-amino-7-methoxy-3-carbamoyloxymethyl-3-cephem-4-carboxylic acid in the presence of pyridine to give the title compound.

EXAMPLE 18

7β-{5-[3,3-Bis(diethoxyphosphono)propylamino]-2-thienylacetamido}-7-methoxy-3-carbamoyloxymethyl-3-cephem-4-carboxylic acid 5-(2,2,2-Trichloroethoxycarbonylamino)-2-thienyl-acetic acid is reacted with the benzhydryl ester of 7β-amino-7-methoxy-3-carbamoyloxymethyl-3-cephem-4-carboxylic acid in the presence of dicyclohexyl-carbodiimide. The reaction product, benzhydryl 7β-[5-(2,2,2-trichloroethoxycarbonylamino)-2-thienylacetamido]-7-methoxy-3-carbamoyloxymethyl-3-cephem-4-carboxylate, is treated with zinc dust in 90% formic acid and forms benzhydryl 7β-(5-amino-2-thienylacetamido)-7-methoxy-3-carbamoylmethyl-3-cephem-4-carboxylate. Reaction with Cl-(CH₂)₂-Z'(tetraethyl 3-chloro-1,1-propanediphosphonate) as described in Example 15, followed by cleavage of the benzhydryl ester as described in Example 14, yields 7β-{5-[3,3-bis(diethoxyphosphono)-propylamino]-2-thienylacetamido}-7-methoxy-3-carbamoyloxymethyl-3-cephem-4-carboxylic acid.

EXAMPLE 19

7β-(2-thienylacetamido)-7-methoxy-3-{[3,3-bis (diethoxyphosphono)-1-propylcarbamoyl]-oxymethyl}-3-cephem-4-carboxylic acid Reaction of tetraethyl 3-chloropropane-1,1-diphosphonate with sodium azide in acetone forms tetraethyl 3-azidopropane-1,1-diphosphonate, which is hydrogenated over Pt at room temperature under 1 bar of hydrogen to tetraethyl 3-aminopropane-1,1-diphosphonate. The benzhydryl ester of 7β-(2-thienylacetamido)-7-methoxy-3-hydroxymethyl-3-cephem-4-carboxylic acid is reacted first with phosgene and then with tetraethyl 3-aminopropane-1, 1-diphosphonate to give the title compound.

EXAMPLE 20

4-Methoxy-6,7,9,11-tetrahydroxy-9-[3,3-bis(diethoxyphosphono)propanoyloxyacetyl]-5,7,8,9,10,12-hexahydrotetracene-5,12-dione 4-Methoxy-6,7,9,11-tetrahydroxy-9-acetyl-5,7,8,9,10,12-hexahydrotetracene-5,12-dione is prepared as described in U.S. Pat. No. 3,803,124 and the hydroxyl groups are protected as (2-methoxyethoxy)-methyl ethers by reaction with (2-methoxyethoxy)-methyl chloride, $CH_3$—O—$CH_2$—$CH_2$—O—$CH_2$—Cl. The 4-methoxy-6,7,9,11-tetra-[(2-methoxyethoxy)-methoxy]-9-acetyl-5,7,8,9,10,12-hexahydrotetracene-5,12-dione thus formed is converted to the 9-bromoacetyl derivative by reaction with bromine in methanol solution, and to the 9-hydroxyacetyl derivative as described for the non-etherified compounds in U.S. Pat. No. 3,803,124. Reaction with 3,3-bis(diethoxyphosphono)-propanoyl chloride and pyridine affords 4-methoxy-6,7,9,11-tetra-[(2-methoxyethoxy)-methoxy]-9-[3,3-bis(diethoxyphosphono)-propanoyloxyacetyl]-5,7,8,9,10,12-hexahydrotetracene-5,12-dione. Deprotection is accomplished by reaction with fluoroboric acid, as described by Ikota et al., *J. Chem. Soc. Chem. commun.* 1978, 869, and yields 4-methoxy-6,7,9,11-tetrahydroxy)-9-[3,3-bis(diethoxyphosphono)-propanoyloxyacetyl]-5,7,8,9,10,12-hexahydrotetracene-5,12-dione.

EXAMPLE 21

4-Methoxy-6,7,9,11-tetrahydroxy-9-[3,3-bis(diethoxyphosphono)propanoyl]-5,7,8,9,10,12-hexahydrotetracene-5,12-dione 4-Methoxy-6,7,9,11-tetra-[(2-methoxyethoxy)-methoxy]-9-bromoacetyl-5,7,8,9,10,12-hexahydrotetracene-5,12-dione, prepared as in Example 20 is reacted with the sodium salt of tetraethyl methylenediphosphonate prepared as quoted in Example 2, above, to give after deprotection as in Example 18, above, 4-methoxy-6,7,9,11-tetrahydroxy-9-[3,3-bis-(diethoxyphosphono)-propanoyl]-5,7,8,9,10,12-hexahydrotetracene-5,12-dione.

EXAMPLE 22

7-(4-Methylpiperazino)-1-cyclopropyl-3-[(2,2-diethoxyphosphono-2-diisopropoxyphosphono-1-oxo]-1-ethyl}-4-oxo-1,4-dihydro-1,6-naphthyridine Diethylchloromethylphosphonate is prepared according to German patent 1,211,200 and is reacted with triisopropylphosphite to give P-diethyl,P'-diisopropylmethylenediphosphonate. The sodium salt of this diphosphonate is generated as quoted in Example 2 above, and reacted with the acid chloride of 7-(4-methylpiperazino)-1-cyclopropyl-4-oxo-1,4-dihydro-1,6-naphthyridine-3-carboxylic acid as described in Example 9 above to yield after product purification 7-(4-methylpiperazino)-1-cyclopropyl-3-[2-diethoxyphosphono-2-diisopropoxyphosphono)-1-oxo)-1-ethyl]-4-oxo-1,4-dihydro-1,6-naphthyridine.

EXAMPLE 23

7β-{(α-Z-Methoxyimino)-[2-(3,3-(diphosphono-propanoylamino)-thiazol-4-yl-acetamido]-3-acetoxymethyl-3-cephem-4-carboxylic acid 7β-{(α-Z-Methoxyimino)-α-[2-(3,3-bis(diethoxyphosphono)-propanoylamino)-thiazol-4-yl-acetamido]-3-acetoxymethyl-3-cephem-4-carboxylic acid, prepared as in Example 16, above, is reacted with an excess of bromotrimethylsilane in dry $CCl_4$ solution, as described in *J. Org. Chem.* 1986, 51, 3488, treated with methanol and then with water as described in the same reference, to give after product purification 7β-{(∝-Z-methoxyimino)-[2-(3,3-(diphosphono-propanoylamino)-thiazol-4-yl-acetamido]-3-acetoxymethyl-3-cephem-4-carboxylic acid.

What is claimed is:

1. A compound of the formula A-(V)$_m$-(R) -Z', wherein A is the residue of a pharmaceutically active anti-infective chemical entity, V is O, S, NR', CONR', CO—O, O—CO, O—CO—O, CO—S, S—CO, S—CO—S, NR'—CO, OCO—NR', NR'—CO—O, NR'—CO—NR", CO—NR'—NR", NR'—NR"—CO, NR'—C(=NH)—NR" or NR'—C(=NH)—NH—C(=NH)—NR" wherein R, R' and R" are H or an organic or heteroorganic group, and m and n are each 1, or one of m and n is 0, and Z' is

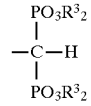

wherein each $R^3$ is independently H, an alkyl or substituted alkyl group of from 1 to about 10 carbons that may be linear or branched, saturated or unsaturated; a cycloalkyl or substituted cycloalkyl group of from 3 to about 10 carbons that may be saturated or unsaturated; a monocyclic or polycyclic aryl group; an aralkyl group or an alkyl group carrying an aryl substituent wherein the alkyl group has from 1 to about 10 carbons that may be linear or branched, saturated or unsaturated; or heterocyclic group selected from pyridine, furan, thiophene, pyrazine, pyrimidine, purine and imidazole.

2. The compound of claim 1 wherein the aryl group is phenyl or naphthyl, optionally substitued by halogen, trifluoromethyl, alkyl of 1 to about 4 carbons, nitro, amino, hydroxy or carboxyl.

3. The compound of claim 1 wherein the residue of the pharmaceutically active compound is selected fron the group consisting of an aminoglycoside, an amphenicol, an ansamycin, a β-lactam, a cycloserine, a aminopyrimidine, a lincosamide, a macrolide, a monobactam, a nitrofuran, an oxacephem, a polypeptide, a quinolone, a quinolone analog, a sulfonamide, a sulfone and a tetracycline.

4. The compound of claim 1 wherein V is O, S, NR', CONR', OCO—NR', NR'—CO—NR", CO—NR'—NR", NR—C(=NH)—NR" or NR'—C (=NH)—NH—C(=NH)—NR", the aryl group is phenyl or naphthyl, optionally substitued by halogen, trifluoromethyl, alkyl of 1 to about 4 carbons, nitro, amino, hydroxy or carboxyl.

5. The compound of claim 1 wherein m is 1 and V is a cyclic moiety of the formula

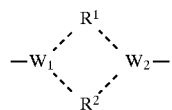

wherein $W_1$ and $W_2$ independently are any atom capable of establishing three or more bonds, and $R^1$ and $R^2$ are hydrocarbon radicals optionally containing at least one heteroatom selected from pyridine, furan, thiophene, pyrazine, pyrimidine, purine and imidazole.

6. The compound of claim 1 wherein R is —$CH_2$.

7. The compound of claim 4 wherein R is —$CH_2$.

8. The compound of claim 1 having the name 6-fluoro-1-ethyl-7-(4-(2,2-diphosphono)-1-ethyl)-1-piperazyl]-4-oxo-1,4-dihydroquinoline-3-carboxylic acid and pharmaceutically acceptable esters thereof.

9. A geminal diphosphonic acid having the name 9-fluoro-3-methyl-10-{4-[3,3-diphosphono)-1-propyl]-1-piperazyl}-7-oxo-2,3-dihydro-7H-pyrido[1,2,3-de][1,4]benzoxazine-6-carboxylic acid, 9-fluoro-3-methyl-10-[4-(4,4-diphosphono-1-butyl)-1-piperazyl]-7-oxo-2,3-dihydro-7H-pyrido[1,2,3-del[1,4]benzoxazine-6-carboxylic acid, 9-fluoro-10-[4-(3,3-diphosphono-1-propyl)-1-piperazyl]-7-oxo-2,3-dihydro-7H-pyrido-[1,2,3-de][1,4]benzoxazine-6-carboxylic acid, 9-chloro-3-methyl-10-[4-(2,2-diphosphono)-1-piperazyl]-7-oxo-2,3-dihydro-7H-pyrido[1,2,3-de]r1,4]-benzoxazine-6-carboxylic acid, 9-fluoro-3-methyl-10-[4-(2,2-diphosphono-1-ethyl)-1-piperazyl]-7-oxo-2,3-dihydro-7H-pyrido[1,2,3-de][1,4]-benzoxazine-6-carboxylic acid, 9-fluoro-3-methyl-10-(3,3-diphosphono-1-propylamino)-7-oxo-2,3-dihydro-7H-pyrido[1,2,3-de][1,4]-benzoxazine-6-carboxylic acid, 9-fluoro-3-(2,2-diphosphono-1-ethyl)-10-(4-methyl-1-piperazyl)-7-oxo-2,3-dihydro-7H-pyrido[1,2,3-de][1,4]benzoxazine-6-carboxylic acid, 9-fluoro-3-methyl-6-(2,2-diphosphono-1-oxo-1-ethyl)-10-(4-methyl-1-piperazyl)-7-oxo-2,3-dihydro-7H-pyrido[1,2,3-de][1,4]benzoxazine, 6-chloro-1-ethyl-7-[4-(3,3-diphosphono-1-propyl)piperazyl]-4-oxo-1,4-dihydroquinoline-3-carboxylic acid, 6-fluoro-1-methyl-7-(4,4-diphosphono-1-butylamino)-4-oxo-1,4-dihydroquinoline-3-carboxylic acid, 6-chloro-1-ethyl-3-[2,2-diphosphono)-1-oxo-1-ethyl]-7-(4-methyl-1-piperazyl )-4-oxo-1, 4-dihydro-quinoline, 6-chloro-7-(4,4-diphosphono)-1-butylamino]-1-methyl-4-oxo-1,4-dihydroquinoline-3-carboxylic acid, 6-fluoro-1-(3,3-diphosphono-1-propyl)-7-(-4-methyl-1-piperazyl)-4-oxo-1,4-dihydroquinoline-3-carboxylic acid, 7-(4-methylpiperazino)-1-cyclopropyl-3-{[(2,2-diphosphono)-1-oxo]-1-ethyl}-4-oxo-1,4-dihydro-1,6-naphthyridine, 1-cyclopropyl-6-fluoro-7-{4-[2,2-diphosphono)-1-ethyl]-1-piperazyl}-4-oxo-1,4-dihydroquinoline-3-carboxylic acid, 1-cyclopropyl-7-[4-(3,3-diphosphono-1-propyl)-1-piperazyl]-4-oxo-1,4-dihydro-1,6-naphthyridine-3-carboxylic acid, 6-fluoro-7-(6,6-diphosphono)- 1-hexylamino )-1-methyl-4-oxo-1,4-dihydroquinoline-3-carboxylic acid, 6-[ (3,3-diphosphono)-propanoyl]amino-3,3-dimethyl-7-oxo-4-thia-1-azabicyclo[3.2.0]heptane-2-carboxylic acid, 7-(4-methylpiperazino)-1-cyclopropyl-4-oxo-1,4-dihydro-1,6-naphthyridine-3-[N-(4,4-diphosphono)-1-butyl)-carboxamide, 7-(4-methylpiperazino)-1-cyclopropyl-3-{[(2-diphosphono)-1-oxo]-1-ethyl}-4-oxo-1,4-dihydro-1,6-naphthyridine, 1-cyclopropyl-6-fluoro-7-[4-(3,3-diphosphono-1-propyl)-1-piperazyl]-1,4-dihydro-4-oxo-quinoline-3-carboxylic acid, 6-[2-ethoxy-5-(3,3-diphosphono-1-propyl)-aminonaphthoyl]-amino-3,3-dimethyl-7-oxo-4-thia-1-azabicyclo[3.2.0]heptane-2-carboxylic acid, 6-[2-ethoxy-3-(3,3-diphosphono-1-propyl)-aminonaphthoyl]-amino-3,3-dimethyl-7-oxo-4-thia-1-azabicyclo[3.2.0]heptane-2-carboxylic acid, 6-[2-ethoxy-4-(3,3-diphosphono-1-propyl)-aminonaphthoyl]-amino-3,3-dimethyl-7-oxo-4-thia-1-azabicyclo[3.2.O]heptane-2-carboxylic acid, 6-[2-ethoxy-6-(3,3-diphosphono-1-propyl)-aminonaphthoyl]-amino-3, 3-dimethyl-7-oxo-4-thia-1-azabicyclo[3.2 .O]heptane-2-carboxylic acid, 6-[2-ethoxy-7-(3,3-diphosphono-1-propyl)-aminonaphthoyl]-amino-3,3-dimethyl-7-oxo-4-thia-1-azabicyclo[3.2.0]heptane-2-carboxylic acid, 7β-[α-(Z-methoxyimino)-α-(2-aminothiazol-4-yl)-acetamido]-3-[(1-methyl-1,2,3-triazol-5-yl)-thiomethyl]-3-cephem-4-[N-(6,6-diphosphono-1-hexyl)-carboxamide], 7β-[α-(Z-methoxyimino)-α-(2-aminothiazol-4-yl)-acetamido]-3-[(4,4-diphosphono-1-butylcarbamoyl)-oxymethyl]-3-cephem-4-carboxylic acid, 7β-[α-(Z-methoxyimino)-α-(2-aminothiazol-4-yl)-acetamido]-3-[(3,3-diphosphonopropanoyloxy)-methyl]-3-cephem-4-carboxylic acid, 7β-[α-(Z-methoxyimino)-α-[2-(3,3-diphosphono-1-propylamino)-thiazol-4-yl]-acetamido}-3-acetoxymethyl-3-cephem-4-carboxylic acid, 7β-{α-(Z-Methoxyimino)-α-[2-(6,6-diphosphono-hexanoyl amino)-thiazol-4-yl ]-acetamido}-3-acetoxymethyl-3-cephem-4-carboxylic acid, 7β-{α-(Z-Methoxyimino)-α-[2-(3,3-diphosphono-propanoylamino)-thiazol-4-yl ]-acetamido}-3-acetoxymethyl-3-cephem-4-carboxylic acid, 6R,7R-7[α-(Z-Methoxyimino)-α-(2-amino-thiazol-4-yl-acetamido]-3-{[2,5-dihydro-6-(3,3-diphosphono-1-propylaminocarbonyloxy)-2-methyl-5-oxo-as-triazin-3-yl]thio-methyl}-3-cephem-4-carboxylic acid, (6R,7R)-7-{α-(Z-Methoxyimino)-α-[2-(2,2-diphosphono-1-ethylamino)-thiazol-4-yl]-acetamido}-3-[2,5-dihydro-6-hydroxy-2-methyl-5-oxo-as-triazin-3-yl)-thio-methyl]-3-cephem-4-carboxylic acid, 7β-[3,3-(diphosphono)-propanoylamino]-7-methoxy-3-carbamoyloxymethyl-3-cephem-4-carboxylic acid, 7β-(5,5-diphosphono-1-perfrylaminocarbonylamino)-7-methoxy-3-carbamoyloxymethyl-3-cephem-4-carboxylic acid, 7β-(6,6-diphosphono-1-hexanoylamino)-7-methoxy-3-carbamoyloxymethyl-3-cephem-4-carboxylic acid, 7β-(2-thienylacetamido)-7-methoxy-3-[(3,3-diphosphono-1-propylcarbamoyl)-oxymethyl]-3-cephem-4-carboxylic acid, 4-methoxy-6,7,9,11-tetrahydroxy-9-[3,3-(diphosphono)propanoyloxyacetyl]-5,7,8,9,10,12-hexahydrotetracene-5,12-dione, 7β-[5-(3,3-diphosphono-1-propylamino)-2-thienylacetamido]-7-methoxy-3-carbamoyloxymethyl]-3-cephem-4-carboxylic acid, 7β-{[5-(3,3-diphosphono-1-propylaminocarbonyl-amino)-2-thienyl]-acetamido}-7-methoxy-3-carbamoyloxymethyl-3-cephem-4-carboxylic acid, 7-azido-7-[(5,5-diphosphono-1-pentylamino)-carbonyl]-3-carbamoyloxymethyl-3-cephem-4-carboxylic acid, 7-azido-7-[(5,5-diphosphono-1-pentylamino)-carbonyl]-3-acetoxymethyl-3-cephem-4-carboxylic acid, 7-(2-thienyl-acetamido)-7-[(5,5-diphosphono-1-pentylamino)-carbonyl]-3-carbamoyloxymethyl-3-cephem-4-carboxylic acid, 4-methoxy-6,7,9,11-tetrahydroxy-9-[(5,5-diphosphono-1-pentylamino)-acetyl]-5,7,8,9,10,12-hexahydro-tetracene-5,12-dione, 4-methoxy-6,7,9,11-tetrahydroxy-9-[(3,3-diphosphono-1-propylaminocarbonyloxy)-acetyl]-5,7,8,9,10,12-hexahydro-tetracene-5,12-dione, 4-methoxy-6,7,9,11-tetrahydroxy-9-(3,3-diphosphono-propanoyloxyacetyl)-S,7,8,9,10,12-hexahydro-tetracene-5,12-dione, 4-methoxy-6,7,9,11-tetrahydroxy-9-[3,3-(diphosphono)propanoyl]-5,7,8,9,10,12-hexahydrotetracene-5,12-dione, or 1,6-bis-{$N_1$:$N_1$'-[4-chloro-3-(2,2-diphosphonoethyl)-phenyl]-diguanido-$N_5$:$N_5$ }-hexane, and the pharmaceutically acceptable mono-, di-, tri- or tetra esters thereof.

10. A pharmaceutical composition of a compound of claim 1 in combination with a pharmaceutically acceptable carrier.

11. A pharmaceutical composition of a compound of claim 2 in combination with a pharmaceutically acceptable carrier.

12. A method of treating osteomyelitis, periodontal disease, urinary tract infections, infectious urinary tract stones, comprising administering a compound of claim 1 in an amount effective to treat said disease.

13. The compound of claim 3 wherein the β-lactam is selected from the group consisting of carbapenems, celophalosporins cephamycins, and penicillins.

14. The compound of claim 1 wherein in any individual compound only one of the following conditions exist:
   (a) both m and n are 0,
   (b) both m and n are 1, or
   (c) one of m and n is 1 and the other is 0.

* * * * *